| United States Patent [19] | [11] 3,963,700 |
|---|---|
| Philip | [45] June 15, 1976 |

[54] RECOVERY OF ANTHOCYANIN FROM PLANT SOURCES

[75] Inventor: Thomas Philip, Tucson, Ariz.

[73] Assignee: University Patents, Inc., Stamford, Conn.

[22] Filed: July 1, 1974

[21] Appl. No.: 484,656

[52] U.S. Cl. ............................ 260/236.5; 426/425; 426/489
[51] Int. Cl.$^2$ ....................... C07G 3/00; A23L 1/27
[58] Field of Search ................ 426/425, 429, , 430, 426/431, 482, 489; 8/80, 53; 260/236.5

[56] References Cited
OTHER PUBLICATIONS

Abstract: "Extraction of Natural Dies From Fruit Pomaces", 73: 44104y, 1969.
Abstract: "Anthocyanin Recovery System From Cranberry Pomace", 73: 43966u, 1970.
Abstract: "Extraction of Anthocyanin Glucosides", 71: 42316d, 1967.
Abstract: "Crystallization and Clarification of Grape Juice", 70: 105208x, 1968.
Abstract: 65: 9629e, "Analytical Value of the Separation of Wine and Grape Juice Anthocyanins by Lead Acetate and Ion Exchange Resins", 1966.

*Primary Examiner*—Frank W. Lutter
*Assistant Examiner*—N. Greenblum
*Attorney, Agent, or Firm*—Mason, Kolehmainen, Rathburn & Wyss

[57] ABSTRACT

A new anthocyanin recovery system from plant materials such as grape wastes based on tartaric acid-alkanol extraction followed by controlled precipitation of excess tartaric acid as potassium hydrogen tartrate is described. An artificial grape drink colored with the anthocyanin extract thus prepared was found to be acceptable.

7 Claims, No Drawings

RECOVERY OF ANTHOCYANIN FROM PLANT SOURCES

This invention relates to the isolation and recovery of anthocyanin from botanical sources, such as grape wastes (pomace). More particularly, it relates to the recovery of anthocyanin from plant materials by extraction with alcoholic tartaric acid solution, followed by precipitation of excess tartaric acid as potassium acid tartrate.

BACKGROUND OF THE INVENTION

The anthocyanins are glycosides of soluble coloring materials of plants. They are water-soluble pigments which are dissolved in the cell sap of plants. The various shades of red, blue, purple and violet of fruits and flowers are due to these pigments. The variations in color are due to slight alterations in the molecule which do not affect the fundamental chemical structure. The anthocyanins are amphoteric and form salts with both acids and bases. They usually occur as mixtures which vary from plant to plant. The color of the pigment is determined by the pH of the medium in which it is dissolved.

As natural products which occur in most fruits and leaves, the anthocyanins are desirable coloring agents for foods and drinks for human consumption. They have very low toxicity which gives them advantages over synthetic coloring agents for food products.

The conventional method of anthocyanin recovery from plant materials involves extraction with dilute alcohol solution of HCl, purification by ion-exchange and acid stabilization (Chiriboga and Franics, J. Am. Soc. Hort. Sci., 95(2):233–236, 1970). The mineral acid used for the elution and stabilization of anthocyanins limits the utilization of extracted anthocyanins due to the low pH imparted when added to food products. Ion-exchange purification is tedious and the cationic resins normally used to purify the anthocyanins also concentrate undesirable metal ions in the recovered anthocyanin. Weak cationic exchangers have low pigment capacity, and strong cationic exchangers, though excellent anthocyanin absorbers, require large volumes of solvent for complete elution of anthocyanins.

This invention has the advantage of avoiding mineral acids and ion-exchange materials which have previously been used in isolating anthocyanins from plants. This specification describes a new procedure for anthocyanin recovery from grape wastes based on tartaric acid-alkanol (methanol) extraction followed by precipitation of excess tartaric acid as potassium hydrogen tartrate. The centrifuge residue and wine grape pomace are wastes generated during the production of grape juice and wine, respectively. Their high anthocyanin and low sugar contents make it possible to recover the anthocyanins by the method described in this specification.

SUMMARY OF THE INVENTION

In accordance with my invention the grape wastes (solids remaining after removal of grape juice and including pomace and other residues from grape juice) are extracted with an alkanol solution of tartaric acid, the concentration of the tartaric acid varying from 0.01% (w/w) to about 2.5% (w/w) depending upon the type of waste used as a starting material. The alkanol can contain one or two carbon atoms and includes methanol and ethanol, preferably in anhydrous condition. The grape wastes are contacted with the alcoholic tartaric acid solution, preferably by leaching in a column, although any other method of contacting the grape waste with the alcohol solution such as agitation in a tank and decanting the supernatant liquid could be used. The alcoholic extract of the grape wastes is clarified, such as by filtration or centrifugation, to remove insoluble materials.

The tartaric acid in the alcoholic extract is then partially neutralized with potassium hydroxide, potassium carbonate, or potassium bicarbonate until approximately 80% to 95% of the tartaric acid is converted to potassium hydrogen tartrate (cream of tartar). The latter is insoluble in the alcoholic solution and precipitates when the solution is at 25°C. or lower. The precipitate of potassium acid tartrate is removed and the resulting alcoholic solution is evaporated, preferably under vacuum at a temperature not greater than 40°C., until the alcohol is removed. The remaining aqueous solution (containing water absorbed from the grape wastes) is then cooled to 15°C. or lower and a further precipitate of potassium acid tartrate is formed which again is removed.

The resulting aqueous solution of the anthocyanin can be used directly as a coloring material for food and drink for human consumption. The pH of the alcoholic solution and the aqueous solution should be maintained at 4 or below during the operations described above to avoid degradation of the anthocyanin.

DETAILED DESCRIPTION OF THE INVENTION

Red wine grape pomace (vinifera) was obtained from E & J Gallo Winery, Modesto, Calif. Centrifuge residues were obtained by clarifying freshly prepared Beauty Seedless grape (vinifera) juice through a centrifuge. Centrifuge residue and pomace had low sugar contents. Both were rich sources of anthocyanins and were wastes generated during the processing of grapes.

The centrifuge residues and pomace were dried in a vacuum oven (80° and 25 inches Hg) to moisture levels below 10% (w/w). Dried centrifuge residue (100 g) was packed in a column (2 × 40 cm) and extracted three times with methanol containing 0.1% (w/w) tartaric acid (100 ml each) at the flow rate of 5 ml per minute. The dried pomace (1 kg) was extracted in the same way with methanol containing 1% (w/w) tartaric acid (1 liter each) in a higher column (6 × 120 cm) and a higher flow rate of 25 ml per minute.

The methanol extracts were partially neutralized with 40% KOH solution so that a residual acidity of 10–15% of total tartaric acid used was maintained to prevent degradation of anthocyanins. The amount of potassium hydroxide required was calculated based on the equation:

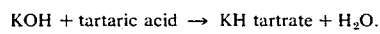

KOH + tartaric acid → KH tartrate + $H_2O$.

The extracts were cooled to 15°C. and the precipitated potassium hydrogen tartrate (cream of tartar) was filtered off. The filtrate was evaporated under vacuum at 40°C. until all the methanol was removed. The aqueous anthocyanin concentrate was cooled to 10°–15°C. and filtered to remove potassium hydrogen tartrate precipitated during concentration.

The properties of the recovered anthocyanin concentrates from centrifuge residues and pomace are summarized in Table 1.

TABLE 1

PROPERTIES OF ANTHOCYANIN CONCENTRATE RECOVERED FROM GRAPE WASTES

| Source | Yield/100 g dry material | Anthocyanin concentration[a] per 100 ml | Soluble solids (° Brix) | Acidity (% tartaric acid) | pH of solution obtained by diluting 1 ml of concentrate with 100 ml of water | Flavor |
|---|---|---|---|---|---|---|
| Centrifuge residue | 15 ml | 0.80 g | 16.0 | 5.6 | 3.1 | None |
| Pomace | 20 ml | 0.65 g | 12.8 | 8.0 | 3.0 | Slight fermented odor |

[a]Anthocyanin concentration was calculated as malvidin 3-glucoside ($E_{1cm}^{1\%}$ = 524.4 in 0.01% conc. HCl/MeOH at 536 nm). Both the concentrates showed absorption maxima at 536 nm in 0.01% conc. HCl/MeOH. The spectral measurements were taken with a Perkin-Elmer 202 UV-Visible Spectrophotometer.

The acceptability of the anthocyanin extract was evaluated by preparing an artificial grape drink (°Brix = 13.0 and pH = 3.0) containing water, sucrose, tartaric acid, artificial grape flavor (Firmenich 59.469/A) and colored with the anthocyanin concentrate. This artificial grape drink colored with the concentrate (1.0 – 1.5 ml concentrate per 100 ml drink) gave a normal red grape juice color which was found to be acceptable by a panel of three judges. The slight fermented flavor of concentrate from pomace was not objectionable in the artificial grape drink. The sugar in the grape wastes is partially extracted by the aqueous alcohol and remains in the aqueous concentrate containing anthocyanin. It is innocuous in coloring agents for beverages. Sugar concentrations of 20% (w/w) in the concentrates are acceptable.

The concentration of tartaric acid required for efficient extraction depends on the material to be extracted. The centrifuge residue can be extracted with a low percentage of tartaric acid, whereas pomace requires higher amounts of tartaric acid. The pomace can be dehydrated with methanol (1 liter/1 kg) instead of drying in an oven without significant loss of anthocyanins. Dehydration with methanol removes part of the flavor associated with fermented pomace. Dehydration of centrifuge residue with methanol results in considerable loss of anthocyanins and should be avoided. The acidity of the final concentrate can be controlled to the desired degree by neutralization of tartaric acid. The two-stage neutralization of acid before and after removal of methanol is preferable to a single neutralization step before the removal of methanol.

This method is amenable to continuous process and the solvent can be recovered and reused. The potassium hydrogen tartrate generated during the recovery process is a valuable by-product. The tartaric acid present in the extract is not objectionable in food products where anthocyanins can be used for coloring.

Because the aqueous concentrate containing anthocyanin contains sugar (usually 5% to 20% w/w) extracted from the grape waste, it is often difficult to prepare a dry anthocyanin product by evaporation of water from the concentrate. Usually the sugar forms a syrup which does not crystallize. In such case, however, a dry powder for use as a coloring agent for beverages can be produced by admixing 1 ml of the concentrate with 15 grams of crystalline sugar. This product can be dissolved in 100 ml of water and produces a satisfactory grape color with sufficient sugar for palatable sweetness for beverage purposes.

In addition to grape wastes, other sources of anthocyanins which can be used as starting materials for this invention include most of the leaf and fruit portions of plants which contain anthocyanins, particularly malvidin glucoside. Other suitable fruit wastes include those from cherries, cranberries and plums, particularly the cherry plum, *Prunus cerasifera*. Particularly valuable as sources of anthocyanins are the fleshy calyxes of roselle, an Indian herb (*Hibiscus sabdariffa*) and the tropical African fruits known as miraculous fruit or miraculous berry which are of the family Sapotaceae, and include *Synsepalum dulcificum* which has a fruit which is a fleshy single-seeded berry, and a herb (*Thaumatococcus daniellii*) of the family Marantaceae whose fruit is a jellylike aril surrounding the seeds. Suitable botanical sources of anthocyanins are also described by Baker et al., Food Product Development, 8, No. 3, 83–87 (1974). Any of the botanical sources of anthocyanins can be treated in accordance with this invention to provide anthocyanin pigments suitable for food and beverage coloring agents.

I claim:

1. A method of separating anthocyanin from botanical sources which comprises drying said botanical sources to a moisture content not greater than 10%, extracting said sources with a solution of tartaric acid in a water-soluble alkanol containing not more than two carbon atoms, neutralizing 80–95% of the tartaric acid in the resulting extract with a potassium compound which reacts with the tartaric acid to yield potassium acid tartrate, removing the potassium acid tartrate from the extract, and then removing the alkanol to form an aqueous anthocyanin concentrate.

2. The method of claim 1 wherein the alkanol is methanol.

3. The method of claim 1 wherein the alkanol is ethanol.

4. The method of claim 1 wherein the tartaric acid solution contains from 0.01% to 2.5% tartaric acid on a weight/weight basis.

5. The method of claim 4 wherein the tartaric acid is partially neutralized with potassium hydroxide.

6. The method of claim 1 wherein the botanical sources is grape solids.

7. The method of claim 5 wherein the aqueous anthocyanin concentrate is cooled to a temperature not greater than 15°C. to precipitate potassium acid tartrate and the latter is removed from the aqueous anthocyanin concentrate.

\* \* \* \* \*